United States Patent [19]

Blank et al.

[11] Patent Number: 4,622,429
[45] Date of Patent: Nov. 11, 1986

[54] PROCESS FOR THE PREPARATION OF SUBSTITUTED BENZALDEHYDES

[75] Inventors: Heinz U. Blank, Odenthal; Erich Wolters, Niederzier; Otto Neuner, Bergisch Gladbach, all of Fed. Rep. of Germany

[73] Assignee: Bayer Aktiengesellschaft, Leverkusen, Fed. Rep. of Germany

[21] Appl. No.: 640,414

[22] Filed: Aug. 13, 1984

Related U.S. Application Data

[63] Continuation of Ser. No. 370,752, Apr. 22, 1982, abandoned.

[30] Foreign Application Priority Data

May 12, 1981 [DE] Fed. Rep. of Germany ....... 3118682

[51] Int. Cl.$^4$ .............................................. C07C 45/49
[52] U.S. Cl. .................................................... 568/428
[58] Field of Search ........................................ 568/428

[56] References Cited

U.S. PATENT DOCUMENTS 1,776,154 9/1930 Knorr et al. ................. 568/428 X
2,158,518 5/1939 Meuly ............................... 568/428
2,158,519 5/1939 Meuly ............................... 568/428
4,195,040 3/1980 Renner ............................. 568/428

OTHER PUBLICATIONS

Crounse, Organic Reactions, vol. 5 (1962), 290-300.
Crounse (I), Jour. Amer. Chem. Soc., vol. 71 (1949), 1263-1264.

Primary Examiner—Bernard Helfin
Attorney, Agent, or Firm—Sprung Horn Kramer & Woods

[57] ABSTRACT

Substituted benzaldehydes are prepared by reaction of the substituted benzenes from which they are derived with carbon monoxide and hydrogen chloride in the presence of metal halides, the process being performed in the presence of 0.5 to 10 mols of hydrogen chloride per mol of metal halide at a partial pressure of carbon monoxide from 1 to 100 bars and a temperature from $-20°$ C. to $+100°$ C. and, if desired, in the presence of an inert diluent. The substituted benzaldehyde which contains, as a substituent, alkyl with at least 2 carbon atoms, cycloalkyl or optionally substituted benzyl, is prepared by reacting the appropriately substituted benzene with the additional presence of a benzene which does not contain the substituents mentioned, but which is identical in respect of further substituents which are optionally present with the benzene from which it is derived.

11 Claims, No Drawings

PROCESS FOR THE PREPARATION OF SUBSTITUTED BENZALDEHYDES

This is a continuation of application Ser. No. 370,752, filed Apr. 22, 1982 and now abandoned.

The invention relates to a process for the preparation of substituted benzaldehydes by reaction of substituted benzenes with carbon monoxide and hydrogen chloride in the presence of a metal halide.

The reaction of, for example, toluene, o-xylene or cumene in the presence of aluminum chloride and copper(I) chloride at a temperature of about 20° to about 50° C. to give the corresponding aldehydes by passing through carbon monoxide and hydrogen chloride (Ann. 347, 347 (1906)) is already known. It is further known that the presence of the copper(I) chloride is unnecessary if, instead of simply passing carbon monoxide through, a raised pressure of CO is used, for example about 21 to 70 bars, temperatures of 25° to 60° C. being described (Org. Reactions 5, 290 (1949)). In both references quoted, the presence of a saturated concentration of hydrogen chloride in the organic reaction medium is reported to be used, which in its absolute amount is very small.

The reference in Org. Reactions points out the difficulties of this reaction due to the formation of byproducts. The appropriate table (page 300 of this reference) shows these difficulties clearly by means of the varying yields for the aromatic aldehydes listed. These difficulties become greater in the transition from benzene to substituted benzenes, particularly in the case of the transition to alkyl-substituted benzenes, and here again particularly for alkyl substituents which contain more than 1 carbon atom.

These difficulties due to the formation of byproducts and insufficient yields in the reaction known as the Gattermann-Koch reaction are confirmed by other references: in J.Am.Chem.Soc. 49, 3150 (1927), it is reported that from ethylbenzene under the conditions of the Gattermann-Koch reaction, only traces of ethylbenzaldehyde were found. In Ber. 66, 1471 (1933), the preparation of cyclohexylbenzaldehyde in a yield of 14 to 16% is reported using the unpressurized variant of this reaction in the presence of copper(I) chloride. U.S. Pat. No. 2,158,519 describes the preparation of cuminaldehyde (p-isopropylbenzaldehyde) at 25° to 30° C. and normal pressure from benzene, i-propyl chloride and carbon monoxide in the presence of $AlCl_3/CuCl$ in a yield of only 25%. Similarly, the preparation of cuminaldehyde is described in J.Am.Chem.Soc. 71, 1263 (1949) by reaction of i-propylbenzene and carbon monoxide under a pressure of 35 bars and at a temperature of 25° to 30° C., a specially conditioned aluminium chloride being employed, and the reaction mixture being saturated with HCl gas before applying the pressure of CO. In this case, a yield of 49%, based on the i-propylbenzene (cumene) employed, is achieved, but in addition, a number of higher alkylated byproducts, for example 31% of diisopropylbenzaldehyde, are found. This large amount of polyalkylated byproducts was obtained in this case, although about 2.3 mols of benzene per mol of isopropylbenzene had been added as a diluent to suppress these higher-alkylated products.

Other higher-alkylated benzenes, in particular those which are branched in the α-position, for example cyclohexylbenzene or cyclopentylbenzene, show a very similar behaviour. The yield of only 49% in the case of cuminaldehyde, already considered above to be poor, is generally still substantially lower in the cases of other alkyl substituents.

These obvious disadvantages and low yields make the variants of the Gattermann-Koch process described uninteresting for industrial application, although substituted aromatic aldehydes are in great demand, in particular in the perfumery industry, but also as generally applicable intermediates. Application in the perfumery industry is indicated in, for example, U.S. Pat. No. 2,158,519, page 1, right-hand column, lines 10/11 and page 3, right-hand column, lines 28/29 and in Römpp, Chemie-Lexikon (Dictionary of Chemistry), Franck'sche Verlagshandlung Stuttgart, 6th Edition 1966, page 1284 (cuminaldehyde). Furthermore, German Offenlegungsschrift No. 2,817,496 indicates the application of such aldehydes as valuable starting materials for dyestuffs, pesticides, plastics and perfumes.

A process has now been found for the preparation of substituted benzaldehydes of the formula

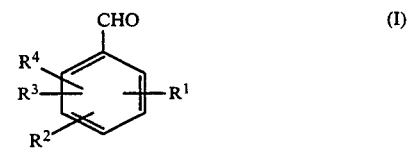

(I)

in which $R^1$ denotes alkyl with at least 2 C atoms, optionally substituted cycloalkyl or optionally substituted benzyl, and $R^2$ is H, F, Cl or Br, or phenyl optionally substituted by F, Cl or Br, $R^3$ is H, $CH_3$, F or phenyl optionally substituted by F, Cl or Br, and $R^4$ is H, F or $CH_3$, and furthermore for the case where $R^3$ and $R^4$ are adjacent, these can together be part of a fused ring, by reacting substituted benzenes of the formula

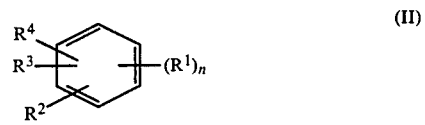

(II)

in which $R^1$ to $R^4$ have the meaning given, and furthermore, for the case that $R^3$ and $R^4$ are adjacent, these can together be part of a fused ring, and n denotes the number 1, 2 or 3, with carbon monoxide and hydrogen chloride in the presence of metal halides, which is characterized in that the reaction is performed in the presence of 0.5 to 10 mols of hydrogen chloride per mol of metal halide under a partial pressure of CO from 1 to 100 bars and at a temperature of −20° C. to +100° C., and, if desired, in an inert solvent, and in the presence of a benzene of the formula

(III)

in which $R^2$, $R^3$ and $R^4$ have the meaning given.

Examples of alkyl with at least 2 C atoms which may be mentioned are branched or straight-chain radicals with 2 to 20, preferably 3 to 10, particularly preferably 3 to 8, C atoms, such as ethyl, propyl, isopropyl, butyl, isobutyl, tert.-butyl, amyl, isoamyl, tert.-amyl, hexyl, heptyl, octyl or decyl. Preferred alkyl radicals are straight-chain and branched alkyls without tertiary C-atoms, Examples of cycloalkyl which may be mentioned are cycloaliphatic radicals with 3 to 8, preferably 5 to 6, ring carbon atoms, which can optionally be further substituted by methyl or ethyl, such as cyclopropyl, cyclobutyl, cyclopentyl, methylcyclopentyl, ethylcyclopentyl, cyclohexyl, methylcyclohexyl, ethylcyclohexyl, cycloheptyl and cyclooctyl.

Substituents of an optionally substituted benzene radical which may be mentioned are one or more halogens, such as F, Cl, Br, I, preferably F, Cl or Br, particularly preferably F or Cl.

The radicals $R^3$ and $R^4$, if they are adjacent, can be part of a fused ring system, for example the indane, tetralin or fluorene system.

The letter n represents the number 1 2 or 3.

Preferably, substituted benzenes of the formula

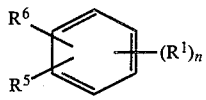 (IV)

in which $R^1$ and n have the meaning given above, $R^5$ represents hydrogen, fluorine, chlorine, bromine or phenyl optionally substituted by fluorine, chlorine or bromine and $R^6$ represents hydrogen, fluorine, methyl, are reacted.

Furthermore, among the substituted benzenes of the formula (IV), those of the formula

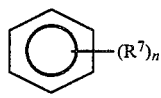 (V)

are particularly preferably employed in which $R^7$ denotes alkyl with at least 2 C atoms or optionally substituted cycloalkyl and n=1, 2 or 3.

Substituted benzenes of the formula (V) with n=1 are very particularly preferably reacted.

Examples of substituted benzenes for the process according to the invention are: ethylbenzene, isopropylbenzene, tert.-butylbenzene, sec.-amylbenzene, tert.-amylbenzene, methylisopropylbenzene, diisopropylbenzene, triisopropylbenzene, cyclopentylbenzene, cyclohexylbenzene, diphenylmethane, fluorene, indane and tetralin.

Preferably: isopropylbenzene, diisopropylbenzene and triisopropylbenzene.

In particular: isopropylbenzene.

Metal halides for the process according to the invention are the substances otherwise known for the Gattermann-Koch reaction, such as aluminum chloride, iron-(III) chloride, antimony pentachloride, tin tetrachloride, CuCl, $CuCl_2$, titanium tetrachloride, zinc chloride and the like, or mixtures of these. Aluminum chloride is preferably employed in the process according to the invention. The metal halide is employed in an amount of from 0.5 to 2 mols, preferably 1.0 to 1.5 mols, per mol of the substituted benzaldehyde of the formula (I), which can be theoretically expected based on the starting amount.

According to the invention, hydrogen chloride is employed in an amount of 0.5 to 10 mols, preferably 0.7 to 5 mols, particularly preferably 1 to 2 mols, per mol of metal halide. For the manipulation of the hydrogen chloride in practice, for example the transfer from a commercial steel pressure cylinder into a pressure reactor for the performance of the process according to the invention, it has been found to be sufficient to measure the amounts of hydrogen chloride mentioned by using its partial pressure in the pressure vessel. For this it was found that on charging a pressure reactor in the temperature range from about 0° C. to room temperature in order subsequently to carry out the process according to the invention, the molar amounts of hydrogen chloride given correspond to about 0.5 to 30 bars, preferably about 1 to 15 bars, particularly preferably about 2 to 5 bars partial pressure of HCl.

The process according to the invention can, for example, be carried out under a partial pressure of carbon monoxide of 1 to 100 bars. Preferably a partial pressure of CO of 2 to 20 bars, particularly preferably 3 to 10 bars is selected.

The reaction temperature can vary within a wide range, for example from −20° C. to +100° C. The reaction is preferably carried out at −15° to +50° C., particularly preferably −10° to +20° C. and very particularly preferably −5° to +15° C.

The process according to the invention can be carried out in the presence or absence of an inert solvent. Examples of such inert solvents which may be mentioned are: halogenated hydrocarbons, such as dichloroethane, trichloroethane, tetrachloroethane or methylene chloride, also carbon disulphide or nitrobenzene. Since an amount of hydrogen chloride exceeding the range mentioned above does not impair the process according to the invention, the process according to the invention can, however, also be performed in excess liquid hydrogen chloride instead of one of the inert solvents mentioned.

The process according to the invention is carried out in the presence of a substituted benzene of the formula (III). This substituted benzene of the formula (III) differs from the substituted benzene of the formula (II), which is to be formulated, by the lack of the substituent $R^1$. For the case where, instead of a substituted benzene of the formula (II) the preferred substituted benzenes of the formula (IV) or the formula (V) mentioned above are employed according to the invention, the reaction is correspondingly carried out in the presence of a substituted benzene, in which the substituent $R^1$ or the substituent $R^7$ corresponding to this $R^1$ is similarly omitted.

This substituted benzene of the formula (III) or the substituted benzenes just described and corresponding to this, which are derived from the formula (IV) similarly by the omission of the substituent $R^1$ and from the formula (V) by the omission of the substituent $R^7$, are employed in the process according to the invention, for example, in an amount from 2 to 20 mols, preferably 2 to 10 mols, particularly preferably 3 to 5 mols per mol of compound of the formula (II), compound (IV) or compound (V) in addition to the amount employed which is required by the stoichiometry, in order to obtain, from the compound of the formula (II), formula (IV) or formula (V) with n-fold substitution, the corresponding compound with only single substitution. The following formula equation using the example of compounds of the formulae (II) and (III) is intended to illustrate this in more detail:

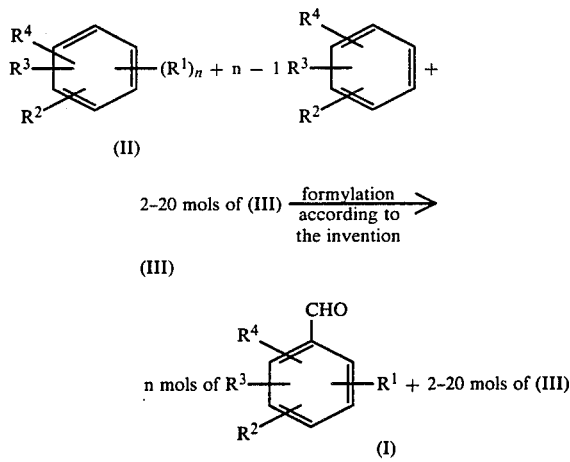

For example, in the case where the index n in the formula (II) has the meaning of 1, 2 to 20 mols of the compound of the formula (III) are employed; in the case where n=2, 3 to 21 mols of the compound of the formula (III) are employed and in the case where n=3, 4 to 22 mols of the compound of the formula (III) are employed. The addition of this amount of substituted benzene of the formula (III) or the substituted benzenes corresponding to this and derived from the formulae (IV) or (V) provide the reaction medium for the formylation according to the invention. In addition, however, for example in the case where the compounds to be reacted and the compounds provided as reaction medium are solid, one or more of the diluents mentioned above can be added as the reaction medium. The amount of this diluent should be such that a homogeneous liquid reaction mixture is obtained at the selected reaction temperature. For example, the diluent or mixture of diluents added is used in an amount from 0.5 to 15 mols per mol of the mixture of compounds of the formulae (II) and (III) or of the preferred reactants derived from these formulae.

In addition it has been found that it is possible, without adversely affecting the formylation according to the invention, to prepare the substituted benzene of the formula (II), (IV) or (V), which is to be formylated, by alkylating a substituted benzene of the formula (III), or a benzene appropriately derived from (IV) or (V) by omission of the radicals $R^1$ or $R^7$, in the reaction mixture with an alkylating agent which is suitable for the introduction of the radical $R^1$ or $R^7$. Examples of such alkylating agents which may be mentioned are the chloride corresponding to the radical $R^1$ or $R^7$, or, when the radical $R^1$ or $R^7$ has an appropriate molecular structure, an olefin on which this radical $R^1$ or $R^7$ is based. A further alkylating agent which may be mentioned is a benzene of the formula (II), (IV) or (V), in which n is larger than 1 and which can transfer one or more radicals $R^1$ or $R^7$. The amount of the chloride or olefin on which the radical $R^1$ or $R^7$ is based is calculated as described above for the molar ratio of metal halide and the substituted benzene which is to be formylated, for example 0.5 to 2.0 mols of metal halide per mol of the chloride or olefin on which the substituent $R^1$ or $R^7$ is based.

The last mentioned reaction variant is performed preferably using one of the olefins on which the radical $R^1$ or $R^7$ is based, or a benzene of the formula (II), (IV) or (V).

The sequence of addition of the reactants is largely arbitrary. For ease of manipulation, it can be advantageous to introduce the solid metal halide first, whilst the liquid, dissolved or gaseous materials can be injected in any desired sequence, for example even into the already closed pressure reactor.

Thus the process according to the invention can be performed, for example in such a way that a stainless steel autoclave, fitted with a stirring device, is charged with the catalyst, the starting material and, if appropriate, the diluent. The mixture is stirred, the chosen temperature is then set and liquid hydrogen chloride is injected via a firmly attached pipe until the desired pressure is reached. Then carbon monoxide is introduced, for example, from a steel pressure cylinder via a reducing valve, until the appropriate pressure is reached, and this pressure is maintained until the end of the reaction. If appropriate, the heat of reaction is removed by a cooling device to the extent necessary for the maintenance of the temperature. The reaction is generally complete when carbon monoxide is no longer consumed, which can be recognized by the pressure of the reaction mixture remaining constant. However, the starting material, if appropriate, with diluent, can also be injected into the mixture of the other components already present, the procedure otherwise being the same.

In the case where the aldehyde is to be produced in the manner described from a benzene lacking $R^1$ or $R^7$ and the olefin on which the radical $R^1$ or $R^7$ is based, such an olefin can be introduced into the reaction mixture, for example, before the addition of carbon monoxide, if appropriate even before the addition of hydrogen chloride.

In the case where the aldehyde is to be produced from the benzene lacking $R^1$ or $R^7$ and the chloride on which the radical $R^1$ or $R^7$ is based, this chloride can be added to the reaction mixture, for example, after introduction of the catalyst and the benzene lacking $R^1$ or $R^7$. In this variant of the reaction, it is advantageous to introduce the hydrogen chloride into the reaction mixture only after addition of the chloride on which the radical $R^1$ or $R^7$ is based. Since in this case, the alkylation of the substituted benzene lacking $R^1$ or $R^7$ leads to the liberation of 1 mol hydrogen chloride per mol of the chloride on which the radical $R^1$ or $R^7$ is based, addition of hydrogen chloride can be completely dispensed with, since, as a result of the alkylation described, this is already present in the reaction mixture in an amount sufficient according to the invention. However, according to the invention, it is quite possible to add further hydrogen chloride to the reaction mixture above that amount produced by the alkylation within the scope of amounts described. The subsequent procedure is then as described above.

A preferred mode of procedure is to place the metal halide, the hydrogen chloride and a reactant suitable for the formation of a partially liquid reaction medium in an autoclave with a stirring device, to set the desired pressure of CO and to start and continue the reaction by injecting the substituted benzene to be formylated or one of the abovementioned alkylating agents which form the substituted benzene to be formylated. The total pressure is thus maintained by continuous metering in of CO. If a substituted benzene of the formula (II), in which $R^1$=H, is formylated, one of the inert solvents mentioned and/or liquid hydrogen chloride is introduced to form a partially liquid reaction medium. If a substituted benzene of the formula (II) is formylated, the corresponding benzene (III) as well as if necessary, excess liquid hydrogen chloride and, if necessary, additionally an inert solvent is introduced to form a partially liquid reaction medium. Then, in order to form the substituted benzene to be formylated, one of the alkylating agents mentioned is injected that is to say a chloride or olefin on which the radical $R^1$ is based, or benzenes of the formula (II), in which n is greater than 1. The reaction in this case can also be started injecting the benzene of the formula (II) with n=1 alone or as a mixture with the alkylating agents mentioned.

For example, for the preparation of cuminaldehyde by this preferred mode of reaction, $AlCl_3$, HCl and benzene are introduced initially in the ratios and amounts described, the desired pressure of CO is established and then, with stirring, propene, isopropyl chloride, cumene, diisopropylbenzene, triisopropylbenzene or a mixture of these is injected.

For working up, the autoclave is depressurized and its content is poured into ice-water to destroy the catalyst. The organic phase is separated off, if appropriate inorganic materials are removed by washing, and the mixture is worked up in the customary manner after removing the diluent, for example by further distillation or by crystallization, to give the substituted benzaldehyde of the formula (I) as the reaction product.

The process according to the invention achieves the object of finding reaction conditions under which the formation of higher alkylated products is suppressed in favour of the monoalkylbenzaldehydes, thus making possible an economical use of the Gattermann-Koch reaction for these aldehydes. Generally, the aldehyde group to be introduced according to the invention goes into the p-position relative to the alkyl radical. The process according to the invention is thus characterized by a very high selectivity in respect of the number of alkyl groups and the position of the aldehyde group to be introduced.

According to the reports of the state of the art, hydrogen chloride was always present in the reaction mixture in an amount which corresponds to its small saturated concentration in this reaction mixture. It is surprising that the advantages found could be achieved by the raising of the amount of hydrogen chloride in the reaction mixture according to the invention.

A further surprising effect of the amount of hydrogen chloride according to the invention in the reaction mixture is the unexpectedly high increase in the reactivity. This means that the reaction time is shortened, that the reaction also proceeds rapidly under very low pressures of carbon monoxide, for example even at 2 to 3 bars, even without the use of auxiliaries, such as copper(I) chloride, and that a reaction still takes place even at temperatures below 0° C., for example at $-10°$ C. A further surprising advantage of the high amount of hydrogen chloride according to the invention is the possibility of employing substituted benzenes with a larger number of alkyl groups, as are obtained in industrial alkylations, without loss of yield in the reaction according to the invention. For example, this applies to the use of di-isopropylated and/or tri-isopropylated and optionally additionally substituted benzenes. This was previously not the case with tri-alkylated benzenes, and also with dialkylated benzenes only if losses in yield of monoalkylated benzaldehyde were accepted.

EXAMPLES 1 TO 10

170.0 g (1.41 mols) of cumene, 327 g (4.19 mols) of benzene and 255 g (1.91 mols) of aluminum chloride are placed in a 1.3 liter V4A steel autoclave and, while stirring, brought to the temperature T(°C.) given in the table. Then the amount of liquid hydrogen chloride given in the table is injected. To the resulting HCl pressure $p_{HCl}$ (bars), the indicated pressure of carbon monoxide $p_{CO}$ (bars) is added, and the resulting total pressure is maintained until the end of take-up of carbon monoxide in the indicated reaction time t (hours) by passing more carbon monoxide in. After allowing the gases to escape, the contents of the autoclave are poured onto ice-water, the organic phase is isolated, distilled and the yield of monoisopropylbenzaldehyde, and the sum of the di- and triisopropylbenzaldehydes, determined and given as a percentage of the theoretical yields, based on cumene employed. The monoisopropylbenzaldehyde contains 97 to 98% of 4-isopropylbenzaldehyde and 2 to 3% of 2- and 3-isopropylbenzaldehyde. In addition, principally 2,4-diisopropylbenzaldehyde and 2,4,6-triisopropylbenzaldehyde are produced.

The Examples 1–3 are not according to the invention (comparison examples).

|     |                                    |                   |                  |          |            | % of theoretical yield      |                                           |
|-----|------------------------------------|-------------------|------------------|----------|------------|-----------------------------|-------------------------------------------|
| No. | Mols of HCl per mols of $AlCl_3$   | $p_{HCl}$ (bars)  | $p_{CO}$ (bars)  | T (°C.)  | t (hours)  | Isopropyl benzaldehyde      | Di- and tri- isopropylbenz- aldehyde      |
| 1   | 0                                  | 0                 | 5                | 15       | 38         | 45                          | 33                                        |
| 2   | 0                                  | 0                 | 20               | 15       | 16         | 44                          | 40                                        |
| 3   | 0                                  | 0                 | 100              | 15       | 2.5        | 51                          | 36                                        |
| 4   | 1                                  | 2                 | 3                | 5        | 7          | 67                          | 16                                        |
| 5   | 3                                  | 7                 | 3                | 5        | 8          | 74                          | 16                                        |
| 6   | 5                                  | 11                | 9                | 5        | 4          | 77                          | 13                                        |
| 7   | 6                                  | 13                | 7                | 5        | 3          | 75                          | 11                                        |
| 8   | 0.5                                | 0.5               | 19               | 5        | 15         | 47                          | 41                                        |
| 9   | 2                                  | 4                 | 20               | $-10$    | 7          | 62                          | 13                                        |
| 10  | 1.5                                | 3                 | 17               | 40       | 4          | 53                          | 17                                        |

EXAMPLE 11

300 ml (7.0 mols) of liquid hydrogen chloride are injected onto 204.0 g (1.53 mols) of $AlCl_3$ in a 1.3 liter V4A steel autoclave. The pressure of hydrogen chloride of 27 bars at 3° C., is increased by an additional pressure of 12 bars of CO, so that the total pressure is 39 bars. Cumene is injected with stirring in the course of 50 minutes. The temperature is kept at approx. 5° C. by appropriate cooling. After a further 10 minutes reaction time, the mixture is worked up as in Examples 1 to 10. The yield of monoisopropylbenzaldehyde is 58% of the theoretical yield. In addition 28% of di- and tri-isopropylbenzaldehydes are obtained.

EXAMPLE 12 (Comparison example)

495 g (4.11 mol) of cumene saturated with hydrogen chloride and 255 g (1.91 mol) of aluminum chloride are placed in a 1.3 liter V4A steel autoclave and, while stirring at 3° C. a CO-pressure of 12 bars is maintained for 43 hours. The mixture is worked up as in the other examples.

The yield of monoisopropylbenzaldehyde is 27.5 g (13.5%). In addition are obtained 57.0 g (42.5%) diisopropylbenzaldehyde and 109.0 g triisopropylbenzaldehyde.

EXAMPLES 13 TO 16

The amounts of di-(DB)- or tri-isopropylbenzene (TB) and benzene (B) given in the table are treated as in Examples 1 to 10. The results can be taken from the table. Example 13 serves as a comparison example.

| No. | 1,3,5-TB (mols) | 1,3-DB (mols) | 1,4-DB (mols) | B (mols) | T (°C.) | Mols of HCl / Mols of AlCl$_3$ | $p_{HCl}$ (bars) | $p_{CO}$ (bars) | t (hours) | Benzaldehydes (% of theoretical yield) | |
|---|---|---|---|---|---|---|---|---|---|---|---|
| | | | | | | | | | | Monoisopropyl | Di- and tri- isopropyl |
| 13 | 0.47 | — | — | 5.13 | 5 | 0 | 0 | 3 | 20 | 0.5 | 1.5 |
| 14 | 0.47 | — | — | 5.13 | 5 | 2 | 4 | 3 | 20 | 71 | 13 |
| 15 | — | 0.7 | — | 4.9 | 5 | 1 | 2 | 3 | 20 | 64 | 14 |
| 16 | — | — | 0.7 | 4.9 | 5 | 3 | 6 | 3 | 20 | 71 | 14 |

EXAMPLES 17 TO 20

In each case, 1.4 mols of the starting materials listed in the table are reacted as in Examples 1-10 at 5° C. and under a pressure of 5 bars of hydrogen chloride and 5 bars of carbon monoxide. The yields of monoalkylbenzaldehyde and the sum of the di- and tri-alkylbenzaldehydes are given in the table.

| | Yield in % of theory | | |
|---|---|---|---|
| No. | Starting material | Monoalkyl-benz-aldehyde | Di- and tri- alkylbenz-aldehydes | Boiling point of the monoalkyl benzaldehyde |
| 17 | Ethylbenzene | 73 | 15 | 120–122° C./44 mbars |
| 18 | Cyclopentene + benzene | 43 | 43 | 95–101° C./0.4 mbar |
| 19 | Cyclohexylbenzene | 68 | 22 | 132° C./2.2 mbars |
| 20 | Indane | 87 | <1 | 143° C./32 mbars |

EXAMPLE 21

452 g (5.8 mols) of benzene and 255 g (1.91 mols) of AlCl$_3$ are placed initially in the autoclave. At 5° C. with stirring, hydrogen chloride is injected until the pressure is 7 bars. A pressure of 3 bars of carbon monoxide is added to this pressure. In the course of an hour, 58.9 g (1.4 mols) of propene are then injected. Thereafter, the total pressure of 10 bars is maintained by passing in CO until no more take-up of CO occurs. This takes about 24 hours. The working-up is as in Examples 1 to 10. 73% of monoisopropylbenzaldehyde and 18% of di- and tri-isopropylbenzaldehyde are obtained, in each case based on the theoretical yield.

EXAMPLE 22

452 g (5.8 mols) of benzene and 255 g (1.91 mols) of AlCl$_3$ are placed initially in the autoclave. At 5° C. under a pressure of 6 bars of CO, 110 g (1.4 mols) of isopropyl chloride are injected in the course of one hour with stirring. CO is passed in via a reducing valve at such a rate that the pressure is constant at 6 bars. After 18 hours, no more CO is taken up. The working-up is carried out as in the previous Example. 157 g of monoisopropylbenzaldehyde are obtained. This corresponds to 75% of theory. In addition, 16% of the theory of di- and triisopropylbenzaldehyde are obtained.

What is claimed is:

1. A process for the preparation of a substituted benzaldehyde of the formula

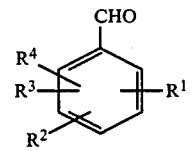

wherein
R$^1$ is selected from the group consisting of alkyl with 2 to 10 C atoms, substituted cycloalkyl and benzyl,
R$^2$ is selected from the group consisting of H, F, Cl, Br, unsubstituted phenyl, phenyl substituted by F, phenyl substituted by Cl and phenyl substituted by Br,
R$^3$ is selected from the group consisting of H, F, unsubstituted phenyl, phenyl substituted by F, phenyl substituted by Cl and phenyl substituted by Br,
R$^4$ is selected from the group consisting of H, F, or, in the case where R$^3$ and R$^4$ are adjacent, R$^3$ and R$^4$ together from a fused ring,
which process comprises contacting a substituted benzene of the formula

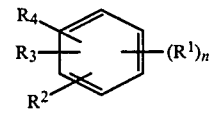

wherein
R$^1$ to R$^4$ have the meanings given above and
n denotes the number 1, 2 or 3,
with carbon monoxide and hydrogen chloride in the presence of a metal halide, the metal halide being employed in an amount of 1.0 to 1.5 mols per mol of substituted benzaldehyde expected to be produced, the hydrogen chloride being present in an amount of 0.5 to 10 mols of hydrogen chloride per mol of metal halide and the carbon monoxide being present at a partial pressure of 2 to 20 bars, at a temperature from −20° C. to +100° C., in the presence of a benzene of the formula

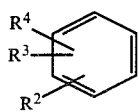

wherein $R^2$, $R^3$ and $R^4$ have the meanings given above.

2. A process according to claim 1, wherein the hydrogen chloride is present in an amount of 0.7 to 5 mols per mol of metal halide.

3. A process according to claim 1, wherein 1 to 2 mols of hydrogen chloride are employed per mol of metal halide.

4. A process according to claim 1, wherein the process is carried out at a temperature of −15° to +50° C.

5. A process according to claim 1, wherein the process is carried out at a temperature of from −10° to +20° C.

6. A process according to claim 1, wherein the process is carried out at a temperature of from −5° to +15° C.

7. A process according to claim 1, wherein said benzene of the formula

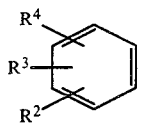

is employed in an amount of (n−1) mols plus an additional 2 to 20 mols per mol of benzene compound of the formula

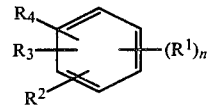

wherein
n and the radical $R^1$ to $R^4$ have the meaning given in claim 1.

8. A process according to claim 1, wherein the carbon monoxide is present at a partial pressure of from 3 to 10 bars.

9. A process according to claim 1, wherein the process is conducted in the presence of an inert solvent.

10. A process according to claim 1, wherein the process is conducted in the presence of excess liquid hydrogen chloride.

11. A process according to claim 1, wherein for said $R^1$, said alkyl has 3 to 10 C atoms.

* * * * *